(12) United States Patent
Zhang et al.

(10) Patent No.: US 12,398,104 B2
(45) Date of Patent: Aug. 26, 2025

(54) ODORLESS THIOLS FOR PERMANENT WAVING, STRAIGHTENING AND DEPILATORY APPLICATIONS

(71) Applicant: The Procter & Gamble Company, Cincinnati, OH (US)

(72) Inventors: Guiru Zhang, Lebanon, OH (US); Stephanie Lee Davis, Liberty Township, OH (US); Bryan Patrick Murphy, Loveland, OH (US); David Salloum, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 592 days.

(21) Appl. No.: 15/963,450

(22) Filed: Apr. 26, 2018

(65) Prior Publication Data

US 2018/0312468 A1  Nov. 1, 2018

Related U.S. Application Data

(63) Continuation-in-part of application No. 15/498,566, filed on Apr. 27, 2017, now abandoned.

(51) Int. Cl.

| | |
|---|---|
| A61Q 9/04 | (2006.01) |
| A61K 8/49 | (2006.01) |
| A61Q 5/04 | (2006.01) |
| C07D 213/20 | (2006.01) |
| C07D 213/32 | (2006.01) |
| C07D 213/34 | (2006.01) |
| C07D 213/42 | (2006.01) |
| C07D 213/74 | (2006.01) |

(52) U.S. Cl.
CPC .......... *C07D 213/42* (2013.01); *A61K 8/4926* (2013.01); *A61Q 5/04* (2013.01); *A61Q 9/04* (2013.01); *C07D 213/32* (2013.01); *C07D 213/34* (2013.01); *C07D 213/74* (2013.01); *C07D 213/20* (2013.01)

(58) Field of Classification Search
CPC .......... A61K 8/4926; A61Q 5/04; A61Q 9/04; C07D 213/32; C07D 213/34; C07D 213/74
See application file for complete search history.

(56) References Cited

U.S. PATENT DOCUMENTS

| | | | |
|---|---|---|---|
| 4,134,411 | A | 1/1979 | Yamazaki |
| 5,041,286 | A | 8/1991 | Donnelly et al. |
| 5,116,608 | A | 5/1992 | Yoshioka et al. |
| 5,558,163 | A | 9/1996 | Hollstein |
| 5,589,163 | A | 12/1996 | Neill et al. |
| 5,651,961 | A | 7/1997 | Neill et al. |
| 6,013,249 | A | 1/2000 | Neill et al. |
| 6,302,119 | B1 | 10/2001 | Coope et al. |
| 6,378,530 | B1 | 4/2002 | Rezvani et al. |
| 6,384,063 | B1 * | 5/2002 | Saito ............... C07D 205/04 514/355 |
| 6,495,125 | B2 | 12/2002 | Glenn, Jr. et al. |
| 6,544,499 | B1 | 4/2003 | Glenn, Jr. |
| 7,157,411 | B2 | 1/2007 | Rohde et al. |
| 7,563,289 | B2 | 7/2009 | Eliu |
| 7,585,833 | B2 | 9/2009 | Fadel |
| 7,955,593 | B2 | 6/2011 | Savaides et al. |
| 2002/0012639 | A1 * | 1/2002 | Glenn, Jr. ............ A61K 8/46 424/59 |
| 2003/0024542 | A1 | 2/2003 | Rathnam |
| 2008/0075681 | A1 | 3/2008 | Cassier et al. |
| 2018/0071188 | A1 | 3/2018 | Barhoum et al. |
| 2018/0311134 | A1 | 11/2018 | Zhang et al. |

FOREIGN PATENT DOCUMENTS

| | | |
|---|---|---|
| DE | 4332805 A1 | 8/1994 |
| RU | 2032670 C1 | 4/1995 |
| WO | 2008012731 A2 | 1/2008 |

OTHER PUBLICATIONS

Want Curls. https://www.self.com/story/want-curls-with-less-damage-tr (Year: 2012).*
Sheppeck. Tetrahedron Letters 41 (2000) 5329±5333.*
Sigma Aldrich. https://www.sigmaaldrich.com/catalog/product/aldrich/641022?lang=en&region=US. Copyright 2020.*
Manuszak. J. Soc. Cosmet. Chem., 47, 213-227 (Jul./Aug. 1996).*
Gunaratne, H. Q. Nimal; Nockemann, P.; Seddon, K. R., Ionic liquids for efficient hydrogen sulfide and thiol scavenging, Green Chemistry, 2014, 16(5), 2411-2417.
All Office Actions, U.S. Appl. No. 15/498,566, Published: Feb. 17, 2021.
Database Caplus, Chemical Abstracts Service, Columbus, Ohio, US, Apr. 1, 1959, 1-methyl-3-(3-mercaptomethyl) pyridinium & K.C. Kennard et al. "Dithiocarbamales, I. Quaternary Ammonium Dithiocarbamates", Journal of Organic Chemistry, vol. 24, No. 4, Apr. 1, 1959, pp. 464-469.
Database Registry, Chemical Abstracts Service, Columbus, Ohio, US, Sep. 23, 2004, "1-methyl-3-(3-mercaptoproyl) pyridinium".
PCT International Search Report and Written Opinion for PCT/US2018/029513 dated Aug. 1, 2018.
Robert Rippel: "Mercaptoacetic Acid and Derivates" In: "Ullman's Encyclopedia of Industrial Chemistry", Jun. 15, 2000, Wiley-VCH, Weinheim, pp. 555-558.

* cited by examiner

*Primary Examiner* — David J Blanchard
*Assistant Examiner* — Lori K Mattison
(74) *Attorney, Agent, or Firm* — John G. Powell; Alexandra S. Anoff

(57) ABSTRACT

Described herein is a chemical class of odorless thiols which can serve as reducing agents. This chemical class involves thiols which can be used as reducing agents for permanent styling treatments, depilatory compositions and other applications. The odorless thiols are thiols having a heterocyclic quaternary ammonium salt in their molecule.

12 Claims, No Drawings

ODORLESS THIOLS FOR PERMANENT WAVING, STRAIGHTENING AND DEPILATORY APPLICATIONS

FIELD OF THE INVENTION

Described herein is the design and synthesis of a class of odorless thiols, particularly odorless thiols that are compounds that have in their molecule (a) a pyridine quaternary ammonium salt and (b) an aliphatic thiol functional group or a protected aliphatic thiol functional group.

BACKGROUND OF THE INVENTION

Reducing agents or reductants are substances that take part in chemical reactions by causing other substances to be reduced. During this chemical transformation, the reducing agent is oxidized by giving electrons to the reduced substance. There are various processes that utilize reducing agents. These can include styling hair treatments such as permanent shaping, waving, and straightening as well as depilation, which involves removal of unwanted hair. Wool is also occasionally treated with reducing agents to improve elongation, elasticity and to facilitate its dyeing process.

The permanent shaping and/or alteration of the curvature of keratinous fibers, in particular human hair, by the application of ammonium thioglycolate (perm salt), or sodium thioyylcolate, is known. In order to provide the consumer with the desired waved or straightened hair, an alkaline solution of perm salt is often utilized as the first step of the process. Thioglycolate reducing agent enters the hair shaft and reduces the —S—S— disulfide bond of hair proteins. This step allows hair fibers to relax from their original shape. After hair is set to its desired new wavy patterns or straightened, a formulation containing hydrogen peroxide, an oxidizing agent, is applied to reform the disulfide bonds and oxidize any remaining unreacted thioglycolate.

Permanent waving and straightening products are typically sold in the form of kits containing a relaxing component, e.g., an alkaline solution of a reducing agent, and an oxidizing component, e.g., a hydrogen peroxide solution. In use, the relaxing component is first applied to hair to either create wave patterns or straighten hair by breaking the disulfide bonds in keratin proteins. After waiting a certain amount of time for the perm salt to do the chemistry, the hair is rinsed. Then, an oxidizing cream or gel is applied to reform a good portion of the disulfide bonds and thus fix the new curvature or newly straightened hair.

Chemical depilation is typically done using compositions having a reducing agent and high pH. Thioglycolate reducing agent is typically used to break the disulfide bond. Depilatory compositions are typically sold as gels, mousses, creams, lotions or peelable films. The composition is typically applied directly on skin where undesirable hair needs to be removed. After a certain amount of time, typically 1-10 minutes, the composition is removed by wiping it off the bodily surface. Next, the skin is rinsed to complete the process. The same technology can be used in a shaving cream to help soften facial hair, which makes subsequent shaving go easier and smoother.

Since Arnold F. Willatt first invented the cold perm using thioglycolate in 1938, many attempts have been made by the perming industry to reduce or eliminate the offensive odor associated with the otherwise very effective treatment. Masking with fragrance is typically attempted for all of the compositions that contain thioglycolate and derivatives. However, the offensive thioglycolate odor cannot be completely masked, especially post treatment. Modifying the thioglycolate to reduce its offensive odor has also been tried. Thiols with higher molecular weight are generally less volatile, thus less of it reaches the olfactory cells. However, it would also be more difficult for a bigger molecule to penetrate hair to remain effective. In the case of higher molecular weight thiols, there is also the difficulty of formulating a less polar ingredient in aqueous chassis. One of the ways to address this polarity issue is to include polar functional groups to the molecule in order to make it more water soluble. However, one of the adverse effects for high polarity is lower penetration of the material into the hair fibers. With lower penetration, the efficiency of the thiol is reduced.

Thiols carrying an aliphatic quaternary ammonium cation have also been explored to minimize the sulfurous stench. They are stable at acidic and neutral conditions. Under in-use conditions at high pH, however, these thiols degrade to generate a tertiary amine and a cyclic sulfide, which defeats the purpose of an odor free technology.

There have also been attempts to use cross-linking reagents without the thiol alcohol functionality to replace thioglycolate. The fact that Brazilian perm uses up to 10 wt. % formaldehyde to relax curly hair highlights the desperation of the perming and straightening industry to disassociate itself from the pungent stench of thioglycolate salts. However, the styling benefits of such treatments are not as durable as the reduction-oxidation process achieves. In addition, there are toxicity concerns about the materials used.

Accordingly, there is a need for a solution to using thioglycolates to create desirable hair styles as well as for depilatory compositions without the undesirable in-use experience, including odor.

SUMMARY OF THE INVENTION

1. An odorless thiol compound comprising the following structure:

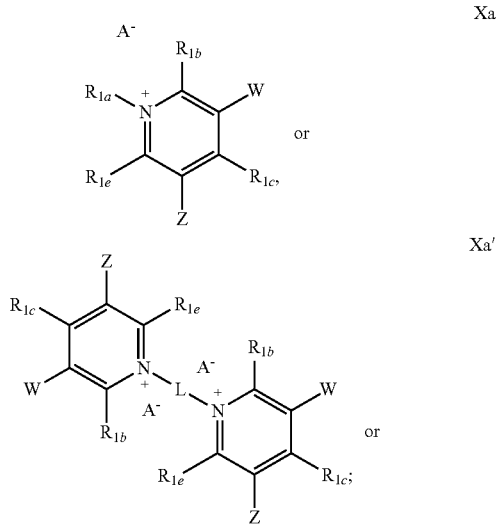

wherein R1a is a linear, branched, cyclo alkyl, aminoalkyl, hydroxyalkyl or alkenyl group, or a linker group L which connects to another moiety of Xa forming a dimeric structure;

wherein L is a linear, branched or cyclo alkyl, aminoalkyl, hydroxyalkyl or alkenyl group;

wherein R1b, R1c, and R1e are each independently selected from hydrogen, alkyl, alkenyl, alkynyl, aryl, hydroxyalkyl, aminoalkyl, acyl, or a heterocyclic moiety;

wherein W and Z are the same or different and are hydrogen or a group T represented by the structure:

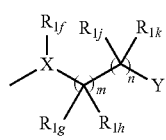

wherein only one of W and Z comprises hydrogen;

wherein, R1f, R1g, R1h, R1j and R1k are each independently selected from hydrogen, alkyl, alkenyl, hydroxyalkyl, thioalkyl, or aminoalkyl;

wherein m and n are independently whole numbers ranging from 0 to 5;

wherein X is selected from CH or N;

wherein Y is SR;

wherein R comprises H or a protected thiol group selected from the group consisting of isothiouronium, thioacetyl, thiotetrahydropyranyl, —C(NH$_2$)=NH$_2^+$A$^-$, a mercapto radical connected to another mercapto radical (Xa) or (Xa') to form a disulfide structure, and combinations thereof;

wherein A$^-$ is selected from the group consisting of bromide, chloride, iodide, sulfate, methanesulfonate, carbonate, phosphate, acetate, and combinations thereof.

DETAILED DESCRIPTION OF THE INVENTION

While the specification concludes with claims which particularly point out and distinctly claim the invention, it is believed the present invention will be better understood from the following description.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. When more than one composition is used during a treatment, as in mixing of the components of a typical perming/straightening product, the total weight to be considered is the total weight of all the compositions applied on the hair simultaneously (i.e. the weight found "on head") unless otherwise specified. The term "weight percent" may be denoted as "wt. %" herein.

The term "alkyl" as used herein refers to a saturated straight or branched carbon chain. Unless specified otherwise, the alkyl group can have from 1 to 30 carbon atoms, or preferably from 1 to 12 carbon atoms, or more preferably from 1 to 6 carbon atoms. The alkyl groups may also contain one or more heteroatoms within the carbon backbone. Examples include oxygen, nitrogen, sulfur, and combinations thereof. The alkyl group may preferably contain between one and four heteroatoms. The alkyl groups may include straight-chain alkyl or branched-chain alkyl. The term "alkyl" includes both "unsubstituted alkyls" and "substituted alkyls", the latter of which refers to alkyl moieties having one or more substituents replacing a hydrogen on one or more carbons of the hydrocarbon backbone. Such substituents may include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

The term "alkenyl" as used herein is an alkyl containing from 2 to 30 carbon atoms and having one or more double bonds. The alkenyl groups may also contain one or more heteroatoms within the carbon backbone. Examples include oxygen, nitrogen, sulfur, and combinations thereof. The alkenyl group may preferably contain between one and four heteroatoms. The alkenyl groups may include straight-chain alkenyl or branched-chain alkenyl, or cycloalkenyl groups. The term "alkenyl" includes both "unsubstituted alkenyls" and "substituted alkenyls", the latter of which refers to alkenyl moieties having one or more substituents replacing a hydrogen on one or more carbons of the hydrocarbon backbone. Such substituents may be the one as set out hereinbefore in the definition of the term "alkyl".

The term "alkynyl" as used herein is an alkyl containing from 2 to 30 carbon atoms and having one or more triple bonds. The alkynyl groups may also contain one or more heteroatoms within the carbon backbone. Examples include oxygen, nitrogen, sulfur, and combinations thereof. The alkenyl group may preferably contain between one and four heteroatoms. The alkynyl groups may include straight-chain alkynyl or branched-chain alkynyl, or cycloalkynyl groups. The term "alkynyl" includes both "unsubstituted alkynyls" and "substituted alkynyls", the latter of which refers to alkynyl moieties having one or more substituents replacing a hydrogen on one or more carbons of the hydrocarbon backbone. Such substituents may be the one as set out hereinbefore in the definition of the term "alkyl".

The term "cycloalkyl" as used herein represents a cyclic version of "alkyl". The term "cycloalkyl" is also meant to include bicyclic, tricyclic and polycyclic versions thereof. Unless specified otherwise, the cycloalkyl group can have 3 to 12 carbon atoms. By analogy, the term "cycloalkenyl" as used herein represents a cyclic version of "alkenyl". The term "cycloalkynyl" as used herein represents a cyclic version of "alkynyl".

The term "heterocyclyl" as used herein refers to a cyclic radical attached via a ring carbon or nitrogen of a monocyclic or bicyclic ring containing 3-10 ring atoms, or preferably from 5-6 ring atoms, containing carbon and one to four heteroatoms each selected from oxygen, sulfur, and N(Y) wherein Y is absent or is hydrogen, oxygen, (C$_{1-4}$) alkyl, phenyl or benzyl, and optionally containing one or more double or triple bonds, and optionally substituted with one or more substituents. Examples of heterocyclic ring include, but are not limited to, benzimidazolyl, benzofuranyl, decahydroquinolinyl, 2H,6H-1,5,2-dithiazinyl, dihydrofuro [2,3-b]tetrahydrofuran, imidazolidinyl, imidazolinyl, morpholinyl, octahydroisoquinolinyl, oxazolidinyl, piperazinyl, piperidinyl, piperidonyl, 4-piperidonyl, pyranyl, pyrazolidinyl, pyrazolinyl, pyrrolidinyl, pyrrolinyl, 2H-pyrrolyl, quinuclidinyl and tetrahydrofuranyl.

The term "halogen" as used herein represents fluorine, chlorine, bromine and iodine.

The term "aryl" as used herein refers to an aromatic monocyclic ring containing 6 carbon atoms, an aromatic bicyclic ring system containing 10 carbon atoms or an aromatic tricyclic ring system containing 14 carbon atoms. Examples are phenyl, naphthyl, phenoxathinyl, piperonyl or anthracenyl, preferably phenyl.

The term "heteroaryl" as used herein refers to from three to ten-membered aromatic ring, preferably a five- or six-membered aromatic ring wherein one or more of the carbon atoms in the ring have been replaced by 1, 2, 3, or 4 (for the five-membered ring) or 1, 2, 3, 4, or 5 (for the six-membered ring) of the same or different heteroatoms, whereby the heteroatoms are selected from the group consisting thereof oxygen, nitrogen, sulfur and mixtures thereof. Examples of the heteroaryl group include groups based on pyrrole, furan, imidazole, pyrazole, oxazole, thiazole, and pyridine. Examples of heteroaryl groups may also include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, chromanyl, chromenyl, cinnolinyl, furanyl, furazanyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, naphthyridinyl, oxadiazolyl, 1,2,3-oxadiazolyl, 1,2,4-oxadiazolyl, 1,2,5-oxadiazolyl, 1,3,4-oxadiazolyl, oxazolyl, oxindolyl, pyrimidinyl, phenanthridinyl, phenanthrolinyl, phenazinyl, phenothiazinyl, phenoxazinyl, phthalazinyl, pteridinyl, purinyl, pyrazinyl, pyrazolyl, pyridazinyl, pyridooxazolyl, pyridinyl, pyrimidinyl, pyrrolyl, quinazolinyl, quinolinyl, 4H-quinolizinyl, quinoxalinyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl and thienyl.

The term "acyl" as used herein refers to an alkanoyl group which is usually derived from a carboxylic acid. Therefore, it has the formula RC(O)—, where R represents an alkyl group that is attached to the C(O) group with a single bond.

The term "carboxylic acid" as used herein refers to the group —COOH. Unless specified otherwise the term "carboxylic acid" embraces both the free acid and carboxylate salt.

The term "substituted" as used herein refers to refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl or alkoxy groups, or any other organic groups containing any number of carbon atoms, preferably $C_{1-14}$ carbon atoms, and optionally include one or more heteroatoms such as oxygen, sulfur, or nitrogen grouping in linear, branched, or cyclic structural formats. Heteroatoms, such as nitrogen, may have hydrogen substituents and/or any permissible substituents of organic compounds described herein that satisfy the valences of the heteroatoms. It is understood that the term "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

As used herein, the term "hair" to be treated may be "living" i.e. on a living body or may be "non-living" i.e. in a wig, hairpiece or other aggregation of non-living keratinous fibers. Mammalian, particularly human, hair is preferred. However, wool, fur, and other keratin containing fibers are suitable substrates for the compositions according to the present invention.

The hair permanent waving or straightening compositions can comprise one or more cationic thiols.

The inventors have surprisingly found that the use of thiols, which have in their molecule (a) a pyridine quaternary ammonium salt and (b) an aliphatic thiol functional group or a protected aliphatic thiol functional group, achieve reduction of the S—S bond of hair proteins without having an objectionable odor.

The disulfide compounds as disclosed herein can be perceived as protected thiols. This is because they can be readily converted to unprotected odorless thiols before their actual use in permanent hair styling or depilatory treatment, by a chemical reaction between another reducing agent with the disulfide compound.

Odorless thiols are described in detail hereinafter. The odorless thiols are a chemical class of reducing agents which are selected from the group containing compounds that can be represented by the following chemical structures

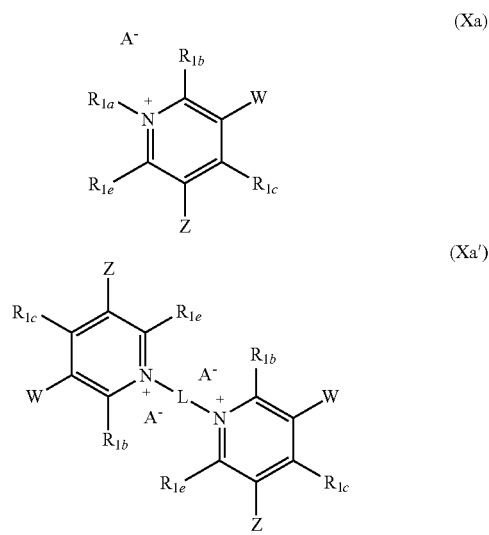

wherein R1a is a linear, branched or cyclo alkyl, aminoalkyl, hydroxyalkyl or alkenyl group, or a linker group L which connects to another moiety of Xa, making it a dimeric structure composed of two pyridinium units, as in Xa';

wherein L is a linear, branched or cyclo alkyl, aminoalkyl, hydroxyalkyl or alkenyl group R1b, R1c, and R1e are each independently hydrogen, alkyl, alkenyl, alkynyl, aryl, hydroxyalkyl, aminoalkyl, acyl, or a heterocyclic moiety;

and wherein W and Z are the same or different and are hydrogen or the group T,

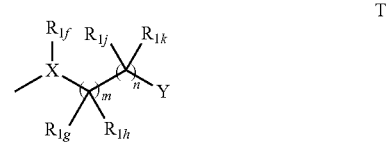

and wherein only one of W and Z can be hydrogen, and the group T is attached to the pyridinium ring through X, and wherein, R1f, R1g, R1h, R1j and R1k are each independently hydrogen, alkyl, alkenyl, hydroxyalkyl, thioalkyl, or aminoalkyl;

wherein m and n are independently whole numbers ranging from 0 to 5;

wherein X is CH or N, and when X is CH, then m+n can be 0 or larger; and when X is a nitrogen atom, then m+n is equal to or larger than 1 and/or equal to or larger than 2;

and wherein Y is R and R can be H or a protected thiol group, which is easily deprotected, such as an (1) isothiouronium group, (2) thioacetyl, (3) thiotetrahydropyranyl, or (4) mercapto radical connected to another mercapto radical (Xa) or (Xa') to form a disulfide structure;

and wherein $A^-$ is an unreactive, non-redox, cosmetically acceptable anion and can be selected from the group consisting of bromide, chloride, iodide, sulfate, methanesulfonate, carbonate, phosphate, acetate, and combinations thereof.

I. Odorless Thiols

Described herein is a general method to derive odorless thiol reducing agents according to the compounds defined herein. Also described herein are methods and compositions for the reshaping of keratin fibers comprising at least one odorless thiol according to the compounds defined herein. Also described herein are methods comprising applying compositions comprising such reducing agents to the keratin fiber for a period of time, followed by an oxidizing agent, to shape the hair and develop the desirable hair style. Also described herein are methods comprising applying compositions comprising such reducing agents to bodily surfaces for a period of time sufficient to remove unwanted hair from the bodily surface.

It is understood that numerous potentially and actually tautomeric compounds are involved. It is to be understood that when this development refers to a particular structure, all of the reasonable additional tautomeric structures are included. In the art, tautomeric structures are frequently represented by one single structure and the disclosure herein follows this general practice.

The typical molecular structure of the reducing agents involves odorless thiols. These odorless thiols can be compounds that have in their molecule (a) a pyridine quaternary ammonium salt and (b) an aliphatic thiol functional group or a protected aliphatic thiol functional group. These compounds do not have an offensive odor, in contrast to the traditionally used thioglycolates, because the presence of the aromatic quaternary ammonium salt in their molecule imparts extremely low volatility. The low volatility contributes to a very low concentration of such compounds in the air and, as a result, the compounds will not be detected by olfactory cells during and after the treatment. The reducing agents are effective reducing agents for use in typical permanent waving, straightening and depilatory applications.

There are additional benefits associated with using odorless thiols under in-use conditions. Hair deposition/penetration can be greatly enhanced compared to thioglycolic acid (TGA) and its salts, which is anionic under in-use conditions. Thus, the reduction efficiency of the odorless thiols is increased. Penetration into live skin cells, however, is reduced as the cell membrane, a lipid bilayer, would only allow a certain cation and anion to go through the ion channels and keep most other salts out. This may result in less skin-irritating treatments.

Previous attempts to link a thiol to an aliphatic quaternary ammonium cation could not deliver an odorless technology at high pH, which is required for the deprotonation of the thiol to make it nucleophilic enough to break the hair protein disulfide bond efficiently. Such aliphatic quaternary ammonium salts can be stable and odorless under acidic and neutral conditions. At high pH, however, compound (III) below can be deprotonated to yield an unstable intermediate (IV), which can undergo a decomposition reaction to produce a tertiary amine (V) and a cyclic sulfide (VI), which can both carry unpleasant odors. The conversion rate of the degradation does not have to be high before the olfactory cells pick up the odor.

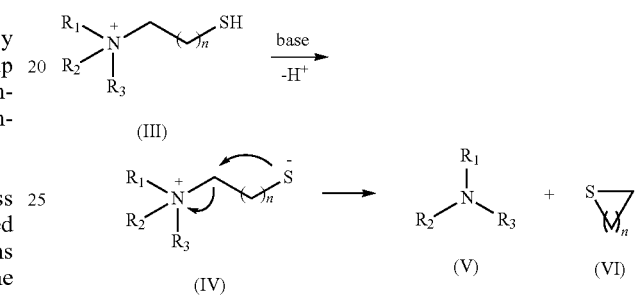

Similar to the above case, not all thiols linked to an aromatic cation are stable, either. Compound (VII) can be stable under acidic and neutral conditions. Under basic conditions, however, it can undergo a degradation reaction through intermediate (VIII) to provide (IX) and thiirane, which can make it an unsuitable candidate for the odor free technology.

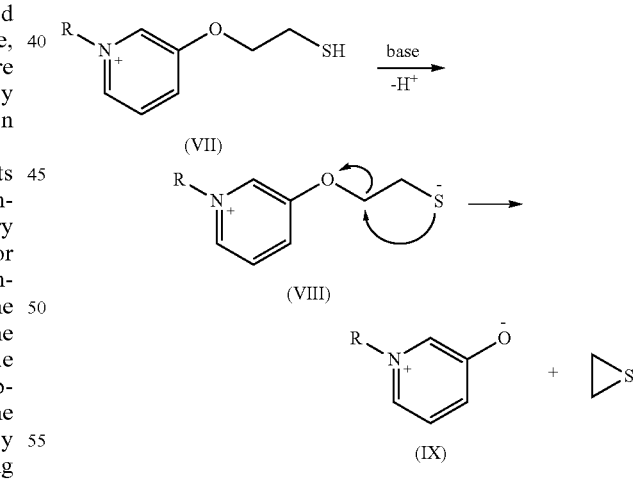

The odorless thiols reducing agents described herein differ from previous approaches in terms of high pH stability and undetectable level of odor. The odorless thiols have in their molecule an aromatic quaternary ammonium salt which contributes to an extremely stable compound at high pH. They are also efficient in breaking the disulfide bonds in keratin fibers. Some members of this class of compounds are three times more efficient than thioglycolate salts. Thus, in these cases substantially equal performance in perming can be achieved with ⅓ molar concentration of the active ingredient compared to the typically used ammonium thioglycolate salt. In addition, the reducing agents disclosed herein have high water solubility as they are organic salts, which makes them easy to formulate in an aqueous chassis. Finally, the reducing agents disclosed herein can pass the odor test in formulation and during on hair applications as stench free.

An example of a subclass of odorless thiols is represented by the following structure

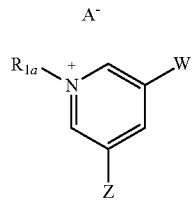

wherein A⁻ is a cosmetically acceptable counterion, wherein R1a is a linear, branched or cyclo alkyl, aminoalkyl, hydroxyalkyl or alkenyl group, and wherein W is hydrogen, alkyl, alkenyl, alkynyl, aryl, hydroxyalkyl, aminoalkyl, acyl or a heterocyclic moiety and Z is group T

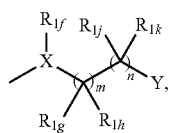

and wherein, R1f, R1g, R1h, R1j and R1k are each independently hydrogen, alkyl, alkenyl, hydroxyalkyl, thioalkyl, or aminoalkyl; and wherein m and n are independently whole numbers ranging from 0 to 5; and wherein X is CH or N and when X is CH then m+n is 0 or larger; and when X is a nitrogen atom, then m+n can be equal or larger than 2 and wherein Y is SH or a protected thiol group, which is easily deprotected, such as an (1) isothiouronium group, (2) thioacetyl, (3) thiotetrahydropyranyl, or (4) mercapto radical connected to another mercapto radical (Xa) or (Xa') to form a disulfide structure.

Examples of compounds in this subclass of odorless thiols are:

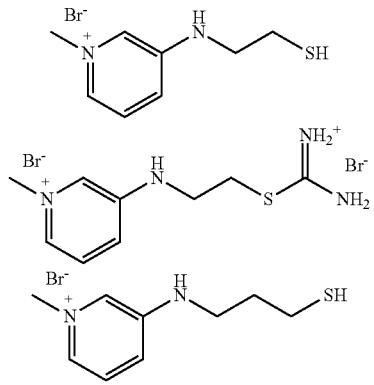

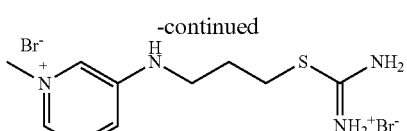

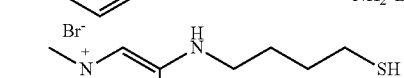

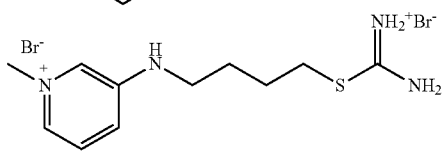

Another example of a subclass of odorless thiols is represented by the following structure:

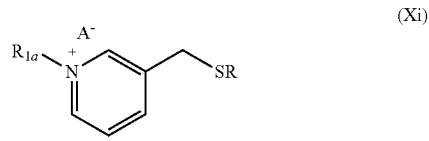

wherein, R1a is linear, branched or cyclo alkyl group, or a linker group L which connects to another moiety of Xi, making it a dimeric structure composed of two pyridinium units joined through the pyridinium nitrogen; and R is hydrogen, acetyl, tetrahydropyranyl, or a mercapto radical connected to another mercapto radical (Xi) to form a disulfide, or the group

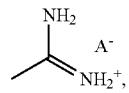

wherein A⁻ is a cosmetically acceptable counterion; and

Examples of compounds in this subclass of odorless thiols are:

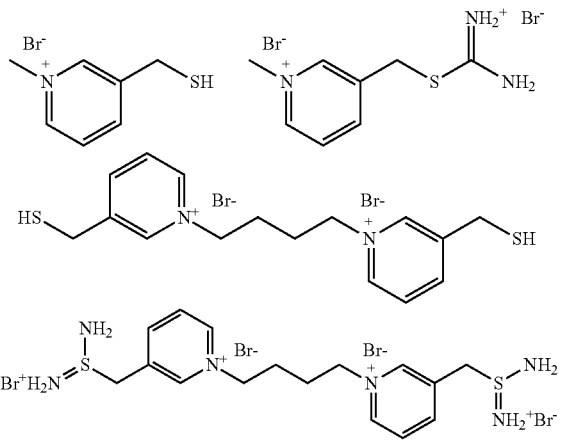

Another example of a subclass of odorless thiols is represented by structure (Xb)

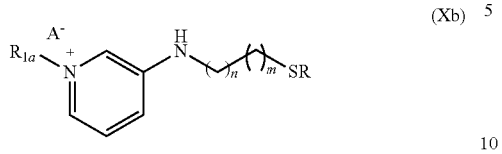 (Xb)

wherein, R1a is linear, branched or cyclo alkyl; and

R is hydrogen, acetyl, tetrahydropyranyl, or a mercapto radical connected to another mercapto radical (Xb) to form a disulfide, or the group

wherein $A^-$ is a cosmetically acceptable counterion; and m and n are independently whole numbers ranging from 0 to 5, and m+n is equal or larger than 2.

Another example of a subclass of odorless thiols is represented by structure (X)

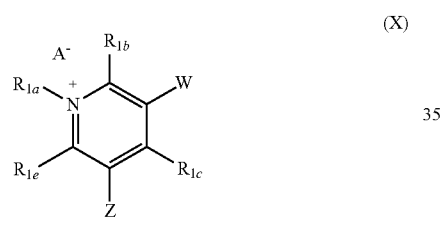 (X)

wherein R1a, R1b, R1c, and R1e are hydrogen;

wherein $A^-$ is a cosmetically acceptable counterion; and both of W and Z are group T

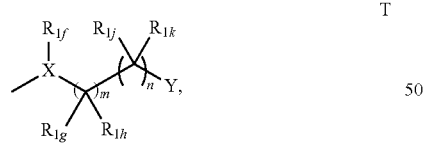 T wherein, R1f, R1g, R1h, R1j and R1k are each independently hydrogen, alkyl, alkenyl, hydroxyalkyl, thioalkyl, or aminoalkyl; and m and n are independently whole numbers ranging from 0 to 5; and X is CH or N. When X is CH, m+n is 0 or larger; and when X is a nitrogen atom, m+n is equal or larger than 2; and and wherein Y is SH or a protected thiol group, which is easily deprotected, such as an (1) isothiouronium group, (2) thioacetyl, (3) thiotetrahydropyranyl, or (4) mercapto radical connected to another mercapto radical (X) to form a disulfide structure.

Another example of a subclass of odorless thiols is represented by structure (Xn)

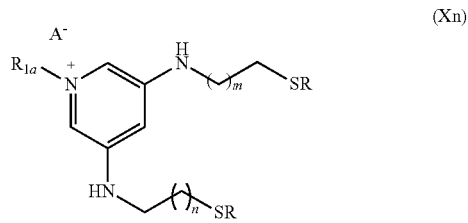 (Xn)

wherein, R1a is linear, branched or cyclo alkyl; and

R is hydrogen, acetyl, tetrahydropyranyl, or a mercapto radical connected to another mercapto radical (Xn) to form a disulfide, or the group

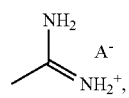

wherein $A^-$ is a cosmetically acceptable counterion; and m and n are independently whole numbers, each ranging from 1 to 5.

Examples of compounds in this subclass of odorless thiols are:

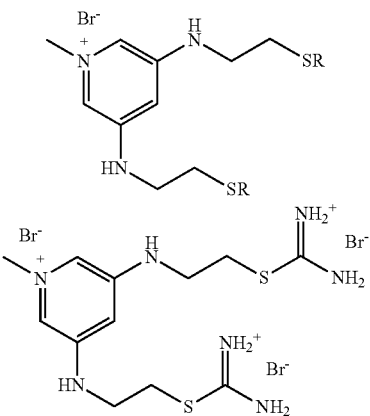

Another example of a subclass of odorless thiols is represented by structure (Xq)

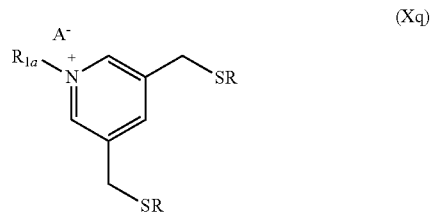 (Xq)

wherein, R1a is linear, branched or cyclo alkyl; and

R is hydrogen, acetyl, tetrahydropyranyl, or a mercapto radical connected to another mercapto radical (Xq) to form a disulfide, or the group

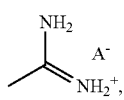

wherein A⁻ is a cosmetically acceptable counterion; and m and n are independently whole numbers ranging from 0 to 5.

Examples of compounds in this subclass of odorless thiols are

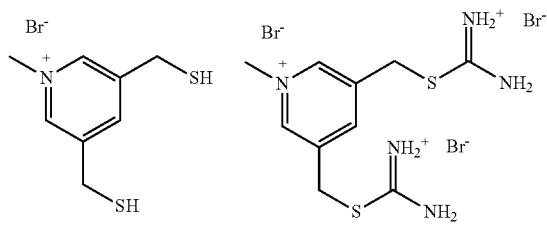

Protecting Groups for Thiols

The odorless thiols described herein can include thiols which have been functionalized with a protective group. A protecting group is a chemical moiety that has been reacted with a functional group of interest (thiol in this case). Such protection is encountered when functional groups are unstable or reactive under certain conditions. Typically, the protected functional group can then be deprotected with a simple transformation to make it again reactive so it can perform a desired function. Non-limiting examples of protecting groups for thiols can include acetyl group, tetrahydropyranyl group, a p-methylbenzyl group, a methoxymethyl group or a —(=NH$_2$⁺)NH$_2$ group. Commonly used protective groups can include trimethylacetamidomethyl, acetamidomethyl group and others. The compounds can also be disulfide compounds, which can be perceived as protected thiols. This is because these compounds can be readily converted to unprotected odorless thiols before their actual use in permanent hair styling or depilatory treatment, by a chemical reaction between another reducing agent with the disulfide compound.

Counterions

The odorless thiols can involve permanent quaternary ammonium salts. Thus, each member of this class of compounds can include at least one anion as a counterion (A⁻). Any cosmetically acceptable counterion, which is unreactive and non-redox, that is it will not take part itself in a redox reaction. Non-limiting typical examples of such anion can include bromide, chloride, iodide, sulfate, methanesulfonate, carbonate, phosphate, and acetate.

Examples

Method of Preparation of Examples of Odorless Thiols

A. Synthesis of 3-(mercaptomethyl)-1-methylpyridin-1-ium trifluoroacetate

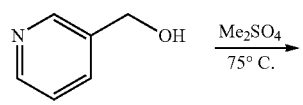

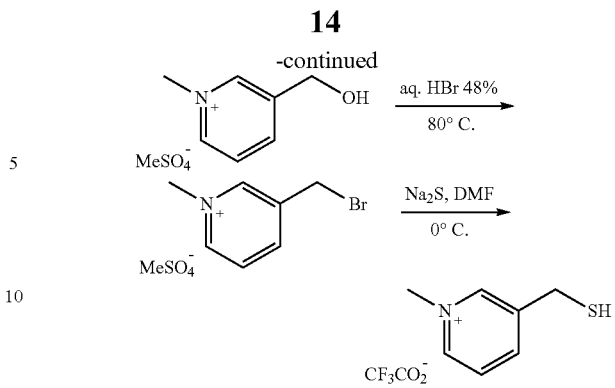

A scintillation vial equipped with silicone septum containing 2.00 g of pyridin-3-ylmethanol in 2.43 g dimethylsulfate is cooled in ice-water bath to 0° C. The reaction mixture is then sealed with screw cap and allowed to warm up to room temperature and above while magnetically stirred. After the temperature rise ceases and the temperature of the reaction mixture drops back to ambient temperature, the reaction mixture is heated to 75° C. in an oil bath. The reaction mixture is kept at 75° C. for 1 hour while magnetically stirred. The resulting thick oil is purified using automated flash column chromatography on silica with dichloromethane and methanol as mobile phase to provide 4.10 g (95% yield) of 3-(hydroxymethyl)-1-methylpyridin-1-ium methylsulfate as a thick colorless oil.

Into a 500 mL round bottom flask, which initially contains 4.10 g 3-(hydroxymethyl)-1-methylpyridin-1-ium methylsulfate, is added a quantity of 150 mL of aqueous HBr (48 weight %). The reaction mixture is then heated to 80° C. while magnetically stirred. Once Liquid Chromatography Mass Spectrometry (LCMS) confirms the complete conversion of the alcohol to the corresponding bromide, the excess aqueous HBr is then removed using vacuum. The residual reddish brown oil is purified using automated flash column chromatography on silica with dichloromethane and methanol as mobile phase to provide 4.31 g (83% yield) of 3-(bromomethyl)-1-methylpyridin-1-ium methylsulfate as a thick amber colored oil.

Into a 100 mL evaporating flask, which initially contains 1.00 g of 3-(bromomethyl)-1-methylpyridin-1-ium methylsulfate, is added 30 mL of anhydrous dimethylformamide (DMF). The solution is then cooled in an ice-water bath. Into the chilled solution is then added a quantity of 0.31 g of sodium sulfide. The reaction mixture is then allowed to warm up to room temperature gradually while being magnetically stirred. The color of the solution becomes dark as the reaction proceeds. Once HPLC confirms that the conversion of the bromide to corresponding mercapto compound has stalled, the reaction is then quenched with 6 mL of a 1 N HCl solution. The solvents are then removed using vacuum. The residual dark brown slurry is purified using automated flash column chromatography on C-18 reverse phase column with water and acetonitrile with 0.1% trifluoroacetic acid (TFA) as mobile phase to provide 0.56 g (60% yield) of 3-(mercaptomethyl)-1-methylpyridin-1-ium trifluoroacetate as white solid.

B. Synthesis of 3-((2-mercaptoethyl)amino)-1-methylpyridin-1-ium trifluoroacetate

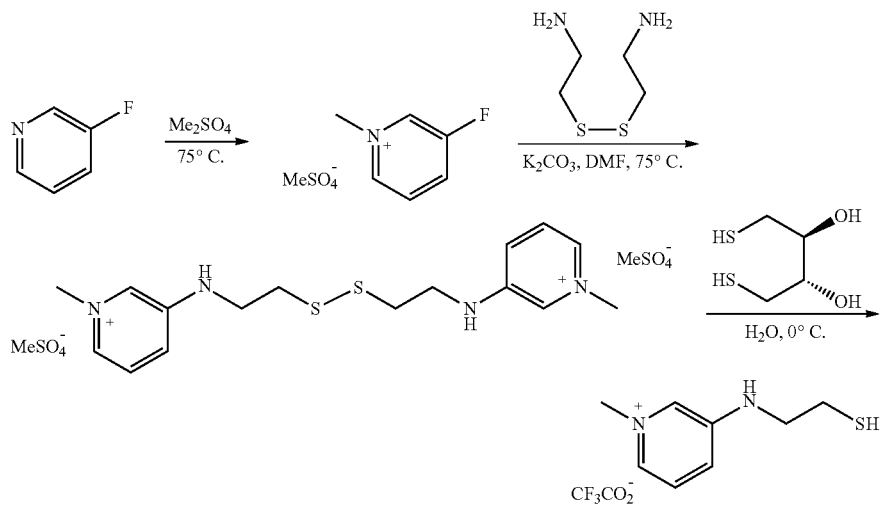

Into a scintillation vial equipped with a silicone septum, which initially contains 3.00 g of 3-fluoropyridine, is added 4.09 g of neat dimethylsulfate. The vial is then sealed and magnetically stirred. After the heat rise ceases and the temperature of the reaction mixture drops back to room temperature, the reaction mixture is heated to 75° C. on oil bath. The reaction mixture is kept at 75° C. for 1 hour while it is magnetically stirred. The resulting thick oil is purified using automated flash column chromatography on silica with dichloromethane and methanol as mobile phase to provide 6.41 g (93% yield) of 3-fluoro-1-methylpyridin-1-ium methylsulfate as a thick colorless oil.

Into a scintillation vial equipped with a silicone septum, which initially contains 1.50 g of 3-fluoro-1-methylpyridin-1-ium methylsulfate dissolved in 10 mL of DMF, is added 1.00 g of potassium carbonate and 0.47 g of 2,2'-dithiobis-ethanamine. The reaction mixture is then heated at 75° C. for 3 hours while magnetically stirred. Once the conversion is confirmed to be complete by Ultra Performance Liquid Chromatography (UPLC), potassium salts are filtered off and the DMF is removed using vacuum. The residual reaction mixture is then purified using automated flash column chromatography on silica with dichloromethane (DCM) and methanol as mobile phase to provide 1.55 g (91% yield) of 3,3'-((disulfanediylbis(ethane-2,1-diyl))bis (azanediyl))bis(1-methylpyridin-1-ium) methylsulfate as a pale yellowish solid.

Into a scintillation vial equipped with a silicone septum, which initially contains 1.00 g of 3,3'-((disulfanediylbis (ethane-2,1-diyl))bis(azanediyl))bis(1-methylpyridin-1-ium) methylsulfate dissolved in 10 mL of water and cooled to 0° C., is added a quantity of 0.33 g of DL-1,4-dithiothreitol. The reaction mixture is magnetically stirred in ice-water bath for 1 hour. Once the conversion is confirmed to be complete by UPLC, the reaction mixture is then purified using automated flash column chromatography on C-18 reverse phase column with methanol/H₂O with 0.1% TFA as mobile phase to provide 0.80 g (79% yield) of 3-((2-mercaptoethyl)amino)-1-methylpyridin-1-ium trifluoroacetate as a pale yellowish solid.

C. Synthesis of 3-[bis(2-mercaptoethyl)amino]-1-methylpyridin-1-ium trifluoroacetate

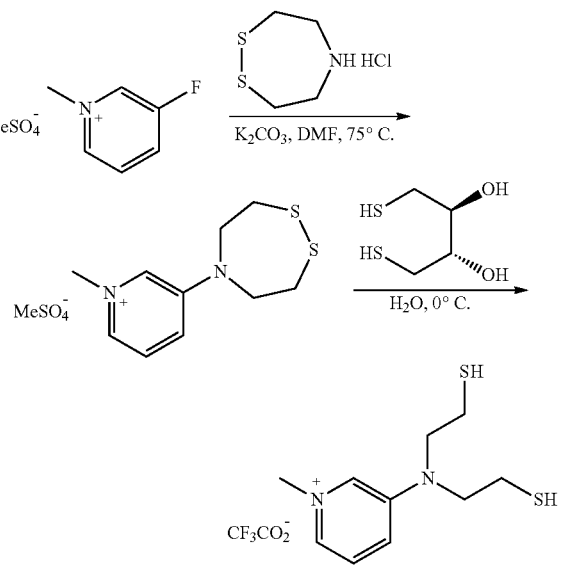

Into a scintillation vial equipped with a silicone septum, which initially contains 1.56 g of 3-fluoro-1-methylpyridin-1-ium methylsulfate dissolved in 10 mL of DMF, is added a quantity of 1.50 g of potassium carbonate and 1.00 g of 1,2,5-dithiazepane hydrochloride. The reaction mixture is then heated to 75° C. and is kept at this temperature for 2 hours while magnetically stirred. Once the conversion is confirmed to be complete by UPLC, the potassium salts are filtered off and the DMF is removed using vacuum. The residual reaction mixture is then purified using automated flash column chromatography on silica with DCM and methanol as mobile phase to provide 1.62 g (82% yield) of 3-(1,2,5-dithiazepan-5-yl)-1-methylpyridin-1-ium methylsulfate as a pale yellowish solid.

Into a scintillation vial equipped with a silicone septum, which initially contains 1.00 g of 3-(1,2,5-dithiazepan-5-yl)-1-methylpyridin-1-ium methylsulfate dissolved in 15 mL of water (15 mL) and cooled at 0° C., is added a quantity of 0.60 g of DL-1,4-dithiothreitol. The reaction mixture is magnetically stirred in ice-water bath for 1 hour. Once the conversion is confirmed to be complete by UPLC, the reaction mixture is then purified using automated flash column chromatography on C-18 reverse phase column with methanol/H$_2$O with 0.1% TFA as mobile phase to provide 0.74 g (73% yield) of 3-[bis(2-mercaptoethyl)amino]-1-methylpyridin-1-ium trifluoroacetate as a pale yellowish solid.

D. Synthesis of 3-((2-((amino(iminio)methyl)thio)ethyl)amino)-1-methylpyridin-1-ium trifluoroacetate

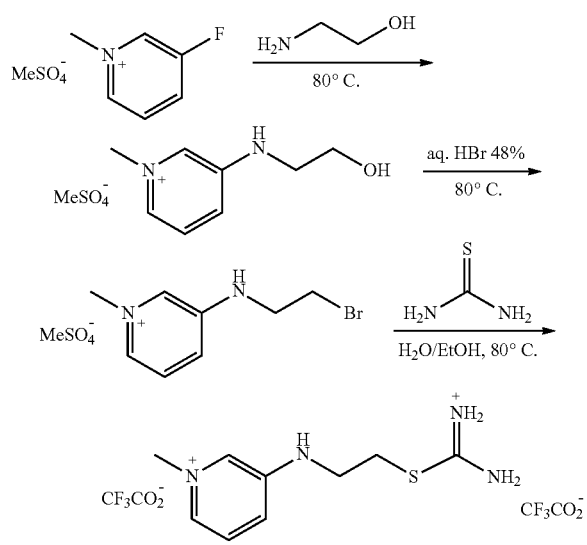

Into a scintillation vial equipped with a silicone septum, which initially contains 3.00 g of 3-fluoro-1-methylpyridin-1-ium methylsulfate and cooled to 0° C., is added a quantity of 2.05 g of neat ethanolamine. The reaction mixture is then heated to 80° C. and is kept at this temperature for 3 hours while magnetically stirred. Once the conversion is confirmed to be complete using UPLC, the reaction mixture is then purified by automated flash column chromatography on silica with DCM and methanol as mobile phase to provide 3.41 g (96% yield) of 3-((2-hydroxyethyl)amino)-1-methylpyridin-1-ium methylsulfate (3.41 g) as a thick colorless oil.

Into a 500 mL round bottom flask, which initially contains 3.41 g of 3-((2-hydroxyethyl)amino)-1-methylpyridin-1-ium methylsulfate, is added a quantity of 150 mL of a aqueous HBr (48% solution). The reaction mixture is then heated to 80° C. while magnetically stirred. Once LCMS confirms the complete conversion of the alcohol to corresponding bromide, excess aqueous HBr is then removed using vacuum. The residual reddish brown oil is purified using automated flash column chromatography on silica with dichloromethane and methanol as mobile phase to provide 3.63 g (86% yield) of 3-((2-bromoethyl)amino)-1-methylpyridin-1-ium methylsulfate as a thick amber colored oil Into a scintillation vial equipped with a silicone septum, which initially contains 1.00 g of 3-((2-bromoethyl)amino)-1-methylpyridin-1-ium methylsulfate dissolved in 20 mL water/ethanol (v/v=1/1), is added a quantity of 0.28 g of thiourea. The reaction mixture is then heated in oil bath to 80° C. and is kept at this temperature for 1 hour while magnetically stirred. Once the conversion is confirmed to be complete by UPLC, the solvents are then removed using vacuum. The residual reaction mixture is then purified using automated flash column chromatography on C-18 reverse phase column with methanol/H$_2$O with 0.1% TFA as mobile phase to provide 1.23 g (92% yield) of 3-((2-((amino(iminio)methyl)thio)ethyl)amino)-1-methylpyridin-1-ium trifluoroacetate as a pale yellowish solid.

E. Synthesis of 1,1'-(butane-1,4-diyl)bis(3-(mercaptomethyl)pyridin-1-ium) bromide

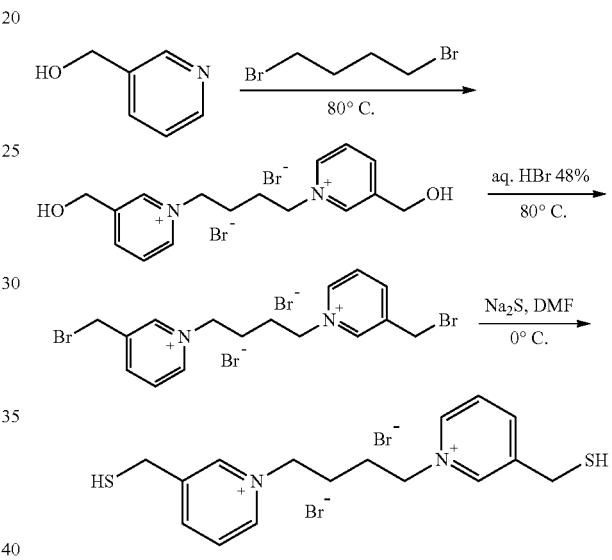

Into a scintillation vial equipped with a silicone septum, which initially contains 3.00 g of pyridin-3-ylmethanol, is added a quantity of 2.00 g of neat 1,4-dibromobutane. The reaction mixture is then sealed with screw cap and heated to 80° C. on oil bath. The reaction mixture is kept at this temperature overnight while it is magnetically stirred. The resulting solid is purified using automated flash column chromatography on silica with dichloromethane and methanol as mobile phase to provide 3.58 g (89% yield) of 1,1'-(butane-1,4-diyl)bis(3-(hydroxymethyl)pyridin-1-ium) bromide as a white solid.

Into a 250 mL round bottom flask, which initially contains 3.00 g of 1,1'-(butane-1,4-diyl)bis(3-(hydroxymethyl)pyridin-1-ium) bromide, is added a quantity of 100 mL of aqueous HBr (48% solution). The reaction mixture is then heated to 80° C. while magnetically stirred. Once LCMS confirms the complete conversion of the alcohol to the corresponding bromide, the excess aqueous HBr is then removed using vacuum. The residual reddish brown oil is purified using automated flash column chromatography on silica with dichloromethane and methanol as mobile phase to provide 3.29 g (85% yield) of 1,1'-(butane-1,4-diyl)bis(3-(bromomethyl)pyridin-1-ium) bromide as a thick amber colored solid.

Into a 100 mL evaporating flask, which initially contains 1.50 g of 1,1'-(butane-1,4-diyl)bis(3-(bromomethyl)pyridin- 1-ium) bromide, is added a quantity of 30 mL of anhydrous DMF. The resulting solution is then cooled in an ice-water bath. Into the chilled solution is then added a quantity of 0.84 g of sodium sulfide. The reaction mixture is then allowed to warm up to room temperature gradually while being magnetically stirred. The color of the solution becomes dark as the reaction proceeds. Once HPLC confirms that the conversion of the bromide to the corresponding mercapto compound has stalled, the reaction is then quenched with 12 mL of a 1N HBr solution. The solvents are then removed using vacuum. The residual dark brown slurry is purified using automated flash column chromatography on C-18 reverse phase column with water and acetonitrile as mobile phase to provide 0.72 g (58% yield) of 1,1'-(butane-1,4-diyl)bis(3-(mercaptomethyl)pyridin-1-ium) bromide as a white solid.

Method of Treating Hair

Reducing Composition

Described herein is a method for treating hair comprising: (a) putting the hair in a desired shape; (b) before and/or after the hair is put in the desired shape, applying a reducing composition to the hair; (c) rinsing the reducing composition from the hair; (d) applying an oxidizing composition to the hair; and (e) rinsing the oxidizing composition from the hair with water.

The reducing composition can comprise from about 2% to about 20%, alternatively from about 2% to about 18%, alternative from about 2.5% to about 15%, alternatively from about 5% to about 13%, alternatively from about 7% to about 12%, and alternatively from about 9% to about 11% of an odorless thiol by weight of the reducing composition. The reducing composition can comprise only the odorless thiol. The odorless thiol can be 3-((2-mercaptoethyl)amino)-1-methylpyridin-1-ium iodide.

The reducing composition can comprise from about 4% to about 10%, alternatively from about 5% to about 7% of a buffering system, by weight of the reducing composition. The buffering system can comprise ammonium carbonate and/or ammonium hydroxide.

Suitable pH modifiers and/or buffering agents can include, but are not limited to: ammonia; alkanolamides (such as monoethanolamine, diethanolamine, triethanolamine, monopropanolamine, dipropanolamine, tripropanolamine, tripropanolamine, 2-amino-2-methyl-1-propanol, 2-amino-2-hydroxymethyl-1,3,-propandiol); guanidium salts; alkali metal and ammonium hydroxides and carbonates; and mixtures thereof.

Further pH modifiers and/or buffering agents can include, but are not limited to: sodium hydroxide; ammonium carbonate; acidulents (such as inorganic and inorganic acids including for example phosphoric acid, acetic acid, ascorbic acid, citric acid or tartaric acid, hydrochloric acid); and mixtures thereof.

The reducing composition can comprise from about 50% to about 93.5%, alternatively from about 55% to about 92.5%, alternatively from about 60% to about 92.5%, alternatively from about 65% to about 92.5%, alternatively from about 70% to about 90% of a solvent, by weight of the reducing composition.

The solvent can be selected from water, or a mixture of water and at least one organic solvent to dissolve the compounds that would not typically be sufficiently soluble in water.

Suitable organic solvents can include, but are not limited to: C1 to C4 lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglocol, polygylcerol); propylene carbonate; and mixtures thereof.

The solvent can also be selected from the group consisting of water, ethanol, propanol, isopropanol, glycerol, 1,2-propylene glycol, hexylene glycol, ethoxy diglycol, and mixtures thereof.

The reducing composition can have a pH of from about 7 to about 11, alternatively from about 8 to about 10.5, alternatively from about 9 to about 10.

The reducing composition can further comprise one or more optional ingredients selected from the group consisting of chelants, radical scavengers, thickeners, rheology modifiers, salt, carbonate ion sources, conditioning agents, surfactants, perfumes, and mixtures thereof.

The oxidizing composition can comprise from about 0.5% to about 12%, alternatively from about 1% to about 8%, and alternatively from about 1% to about 5% of an oxidizing agent, by weight of the oxidizing composition.

The oxidizing agent can be selected from water soluble peroxygen oxidizing agents. Water-soluble peroxygen oxidizing agents can include, but are not limited to, hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulfates and the like. These inorganic perhydrate salts may be incorporated as monohydrates, tetrahydrates etc. Alkyl and aryl peroxides, and or peroxidases, oxidases, and uricases and their substrates may also be used. Mixtures of two or more such oxidizing agents can also be used if desired. The oxidizing agents may be provided in aqueous solution or as a powder which is dissolved prior to use. The oxidizing agents may be selected from the group consisting of hydrogen peroxide, percarbonate, persulfates and combinations thereof.

A potential oxidizing agent for use herein is a source of peroxymonocarbonate ions formed in situ from a source of hydrogen peroxide and a hydrogen carbonate ion source. Moreover, this system can be particularly effective in combination with a source of ammonia or ammonium ions. Accordingly, any source of these peroxymonocarbonate ions may be used. Suitable sources for use herein can include sodium, potassium, guanidine, arginine, lithium, calcium, magnesium, barium, ammonium salts of carbonate, carbamate and hydrocarbonate ions and mixtures thereof such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Percarbonate salts may be used both as an oxidizing agent and as a source of carbonate ions. Sources of carbonate ions, carbamate and hydrocarbonate ions can include sodium hydrogen carbonate, potassium hydrogen carbonate, ammonium carbamate, and mixtures thereof. The oxidizing composition is selected from the group consisting of potassium bromate, sodium bromate, sodium perborate, dehydroascorbic acid, hydrogen peroxide, urea peroxide, and mixtures thereof. The oxidizing agent can be hydrogen peroxide.

The oxidizing composition can comprise from about 80% to about 97%, alternatively from about 85% to about 97%, and alternatively from about 90% to about 95% of a solvent, by weight of the oxidizing composition.

The oxidizing composition can further comprise one or more optional ingredients selected from the group consisting of chelants, radical scavengers, thickeners, rheology modifiers, salt, carbonate ion sources, conditioning agents, surfactants, perfumes, and mixtures thereof.

The method can also be used for hair depilation/removal. Here, the pH of the reducing composition can be from about 8 to about 12, alternatively from about 9 to about 11.5, and alternatively about 10.

The method of treating hair can first comprise separating the hair (which is washed and towel-dried) into multiple sections, and then these sections can be rolled onto curlers (optional for straightening). The curlers used for permanent waves can have a diameter of about 5 mm to about 13 mm, while the curlers used for straightening can have a diameter greater than 13 mm.

After the rolling on curlers is finished, the curlers can be thoroughly wetted down using the required quantity of the reducing composition, which can be from about 60 g to about 120 g.

The amount of time the permanent shaping composition stays on the hair can be from about 1 minute to about 30 minutes, alternatively from about 15 minutes to about 30 minutes. This action time can be shortened by adding heat via the use of a heat radiator or a hood dryer.

After the action time has elapsed that is sufficient for the permanent shaping, which is dependent upon hair quality, the pH value, the shaping effectiveness of the shaping agent, the desired level of change, as well as on the application temperature, the hair is then rinsed with water. Optionally, for straightening, the hair may be dried and then flattened with a heated device such as a flat iron to achieve desired shape.

Thereafter, the hair is oxidatively post-treated ("fixed"). The oxidizing composition can be used in a quantity of from about 50 g to about 200 g, alternatively from about 80 g to about 100 g, depending on hair thickness and length. The concentration of the oxidizing agent can vary depending on application time (normally about 1 minute to about 40 minutes, alternatively about 5 minutes to about 20 minutes) and application temperature (25 deg. C. to 50 deg. C.).

After an action period required for the fixing composition of from about 3 minutes to about 15 minutes, alternatively from about 5 minutes to about 10 minutes, the curlers are removed (if used). It can be advantageous if the hair is then finally shaped as desired and then dried.

EXAMPLES

The following examples illustrate the compositions as described herein. The exemplified compositions may be prepared by conventional formulation and mixing techniques. It will be appreciated that other modifications of the compositions described herein within the skill of those in the art can be undertaken without departing from the spirit and scope of compositions described herein. All parts, percentages, and ratios herein are by weight unless otherwise specified. Some components may come from suppliers as dilute solutions. The amount stated reflects the weight percent of the active material, unless otherwise specified.

Reducing Compositions

| | % by weight |
|---|---|
| Composition A | |
| Odorless thiol[1] | 2.5-15 |
| Ammonium Hydroxide (aq. 28% active) | 4.5 |
| Water | qs to 100 |
| Composition B | |
| Odorless thiol[1] | 2.5-15 |
| Ammonium carbonate | 10 |
| Water | qs to 100 |
| Composition C | |
| Odorless thiol[1] | 2.5-15 |
| FlexiThix ™ [2] | 5 |
| Phenoxyethanol | 0.3 |
| Sodium Benzoate | 0.2 |
| Disodium EDTA | 0.1 |
| Ammonium Hydroxide (aq. 28% active) | 4 |
| Water | qs to 100 |
| Composition D | |
| Odorless thiol[1] | 2.5-15 |
| Aculyn ™ 46[3] | 15.8 |
| Phenoxyethanol | 0.3 |
| Sodium Benzoate | 0.3 |
| Disodium EDTA | 0.1 |
| Ammonium Hydroxide (aq. 28% active) | 4 |
| Water | qs to 100 |
| Composition E | |
| Odorless thiol[1] | 2.5-15 |
| Plantaren ® 2000 N UP[4] | 20 |
| Phenoxyethanol | 0.3 |
| Sodium Benzoate | 0.3 |
| Disodium EDTA | 0.1 |
| Ammonium Hydroxide (aq. 28% active) | 4 |
| Water | qs to 100 |
| Composition F | |
| Odorless thiol[1] | 2.5-15 |
| Foaming agent | 5 |
| Phenoxyethanol | 0.3 |
| Sodium Benzoate | 0.3 |
| Disodium EDTA | 0.1 |
| Ammonium Hydroxide (aq. 28% active) | 4 |
| Water | qs to 100.0% |

[1] The odorless thiol may be any odorless thiol described herein.
[2] PVP polymer supplied by Ashland.
[3] PEG-150/Stearyl/SMDI copolymer supplied by Rohm and Haas.
[4] Chemical makeup supplied by BASF.

Oxidizing Compositions

| | % by weight |
|---|---|
| Composition G | |
| Hydrogen Peroxide | 0.5-12 |
| Water | qs to 100 |
| Composition H | |
| Hydrogen Peroxide | 3 |
| Cetyl/stearyl alcohol | 4 |
| Salicylic acid | 0.1 |
| Phosphoric acid | 0.09 |
| Etidronic acid | 0.01 |
| Fragrance | 0.4 |
| Water | qs to 100 |
| Composition I | |
| Hydrogen Peroxide | 2 |
| Salicylic acid | 0.1 |
| Disodium hydrogen phosphate | 0.2 |
| Phosphoric acid | 0.15 |

-continued

|  | % by weight |
|---|---|
| Ethoxylated castor oil | 1 |
| Vinylpyrrolidone/styrene copolymer | 0.1 |
| Fragrance | 0.1 |
| Water | qs to 100 |

Data

Mannequin Head Odor and Curl Expert Evaluation

Control perm: Omniperm™ with ammonium thioglycolate, available from Zotos Professional®, including both the reducing and oxidizing steps.

Test Perm:

| Reducing Composition | |
|---|---|
| 3-((2-mercaptoethyl)amino)-1-methylpyridin-1-ium iodide | 10 |
| Ammonium carbonate | 5 |
| Ammonium hydroxide | to pH = 9.6 |
| Water | qs to 100 |
| Oxidizing Composition | |
| Hydrogen Peroxide | 3 |
| Cetyl/stearyl alcohol | 4 |
| Salicylic acid | 0.1 |
| Phosphoric acid | 0.09 |
| Etidronic acid | 0.01 |
| Fragrance | 0.4 |
| Water | qs to 100 |

Odor Assessments:

Treatment and expert sensory performed by licensed cosmetologist with 20+ years expertise in perms. All evaluations shown in graphs were done with hair in wet state, before drying. Sulfur odor was zero from the beginning with the test perm treatment. During treatment, the test perm had some ammonia odor from the ammonium hydroxide/carbonate buffer which is represented in Table 1, "Total Odor."

TABLE 1

|  | Sulfur Odor | | Total Odor | |
|---|---|---|---|---|
|  | Scale: 0 (none)-5 (most) | | | |
| WET HAIR EVALUATIONS: | Control Perm | Test Perm | Control Perm | Test Perm |
| Hair processing | 5 | 0 | 5 | 3 |
| After neutralizing | 5 | 0 | 5 | 1 |
| After 1 wash | 4 | 0 | 4 | 0 |
| After 2 washes | 4 | 0 | 4 | 0 |
| After 3 washes | 3 | 0 | 3 | 0 |
| After 4 washes | 3 | 0 | 3 | 0 |
| After 5 washes | 3 | 0 | 3 | 0 |
| After 10 washes | 1 | 0 | 1 | 0 |
| After 15 washes | 1 | 0 | 1 | 0 |
| After 20 washes | 1 | 0 | 1 | 0 |

Curl Retention Assessments:

Treatment and expert sensory performed by licensed cosmetologist with 20+ years expertise in perms. All evaluations shown in graphs were done with hair in dry state, after air drying. Photos are available for most time points as well.

TABLE 2

| AIR DRIED CURL | Curl Retention | |
|---|---|---|
|  | Scale: 0 (none)-5 (most) | |
| EVALUATIONS: | Control Perm | Test Perm |
| After treatment | 5 | 5 |
| After 1 wash | 4 | 4 |
| After 2 washes | 4 | 4 |
| After 3 washes | 4 | 4 |
| After 4 washes | 4 | 4 |
| After 5 washes | 4 | 4 |
| After 10 washes | 4 | 4 |
| After 15 washes | 4 | 4 |
| After 20 washes | 4 | 4 |

Conclusion:

3-((2-mercaptoethyl)amino)-1-methylpyridin-1-ium iodide test treatment provided equal curl retention (data in Table 2) through 20 washes to benchmark control perm but with significantly less odor than control (data in Table 1).

Depilatory Compositions

The depilatory composition can be applied to the skin for 2 or more minutes

A method of removing hair from the bodily surface, the method can comprise the steps of:
  a. Applying the composition to the bodily surface where it is desired to remove hair;
  b. Leaving the composition on the bodily surface for 1 to 15 minutes;
  c. Removing the composition from the bodily surface.

| Ingredient | Weight % |
|---|---|
| Potassium thioglycolate | 5 |
| Xanthan gum | 0.5 |
| Urea | 8 |
| Glycerin | 1 |
| Sodium gluconate | 0.1 |
| C10-30 Alkyl acrylate crosspolymer[1] | 1.5 |
| KOH | To adjust the pH to 11.5 (+/−0.5) |
| Deionized water | QS |

[1]Ultrez 20 supplied by Lubrizol

Combinations:
  A. A method for treating hair comprising:
    a. putting the hair in a desired shape;
    b. before and/or after the hair is put in the desired shape, applying a reducing composition to the hair comprising:
      i. from about 2.5% to about 15% of a cationic mercapto amino pyridinium compound or a cationic dimercapto amino pyridinium compound, by weight of the reducing composition;
      ii. from about 4% to about 10% of a buffering system, by weight of the reducing composition; and
      iii. from about 50% to about 93.5% of a solvent, by weight of the reducing composition;
        wherein the reducing composition has a pH of from about 8 to about 10.5;
    c. rinsing the reducing composition from the hair;
    d. applying an oxidizing composition to the hair comprising:
      i. from about 0.5% to about 12% of an oxidizing agent, by weight of the oxidizing composition; and
      ii. from about 80% to about 97% of a solvent, by weight of the oxidizing composition; and
    e. rinsing the oxidizing composition from the hair.

B. The method according to Paragraph A, wherein the reducing composition comprises from about 55% to about 92.5% of the solvent, by weight of the reducing composition.

C. The method according to Paragraphs A-B, wherein the reducing composition comprises from about 60% to about 92.5% of the solvent, by weight of the reducing composition, preferably from about 70% to about 90% of the solvent, more preferably from about 85% to about 97% of the solvent, by weight of the oxidizing composition, and most preferably from about 90% to about 95% of the solvent.

D. The method according to Paragraphs A-C, wherein the oxidizing agent is hydrogen peroxide.

E. The method according to Paragraphs A-D, wherein the reducing composition comprises from about 5% to about 13% of a cationic mercapto amino pyridinium compound or a cationic dimercapto amino pyridinium compound, by weight of the reducing composition.

F. The method according to Paragraphs A-E, wherein the reducing composition comprises from about 7% to about 12% and preferably from about 9% to about 11% of a cationic mercapto amino pyridinium compound or a cationic dimercapto amino pyridinium compound, by weight of the reducing composition.

G. The method according to Paragraphs A-F, wherein the reducing composition comprises the cationic mercapto amino pyridinium compound.

H. The method according to Paragraphs A-G, wherein the cationic mercapto amino pyridinium compound is 3-((2-mercaptoethyl)amino)-1-methylpyridin-1-ium iodide.

I. The method according to Paragraphs A-H, wherein the reducing composition comprises from about 5% to about 7% of the buffering system, by weight of the reducing composition.

J. The method according to Paragraphs A-I, wherein the reducing composition has a pH of from about 9 to about 10.

K. The method according to Paragraphs A-J, wherein the buffering system comprises ammonium carbonate and ammonium hydroxide.

L. The method according to Paragraphs A-K, wherein the oxidizing composition comprises from about 1% to about 7% of the oxidizing agent, by weight of the oxidizing composition.

M. The method according to Paragraphs A-L, wherein the oxidizing composition comprises from about 1% to about 5% of the oxidizing agent, by weight of the oxidizing composition.

N. The method according to Paragraphs A-M, wherein the reducing composition further comprises one or more optional ingredients selected from the group consisting of chelants, radical scavengers, thickeners, rheology modifiers, salt, carbonate ion sources, conditioning agents, surfactants, perfumes, and mixtures thereof.

O. The method according to Paragraphs A-N, wherein the oxidizing composition further comprises one or more optional ingredients selected from the group consisting of chelants, radical scavengers, thickeners, rheology modifiers, salt, carbonate ion sources, conditioning agents, surfactants, perfumes, and mixtures thereof.

P. An odorless thiol compound comprising the following structure:

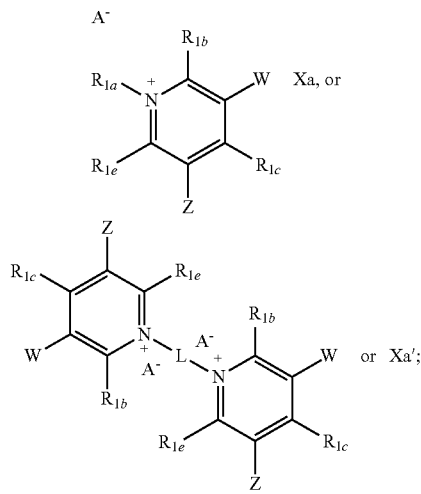

wherein R1a is a linear, branched, cyclo alkyl, aminoalkyl, hydroxyalkyl or alkenyl group, or a linker group L which connects to another moiety of Xa forming a dimeric structure;

wherein L is a linear, branched or cyclo alkyl, aminoalkyl, hydroxyalkyl or alkenyl group;

wherein R1b, R1c, and R1e are each independently selected from hydrogen, alkyl, alkenyl, alkynyl, aryl, hydroxyalkyl, aminoalkyl, acyl, or a heterocyclic moiety;

wherein W and Z are the same or different and are hydrogen or a group T represented by the structure:

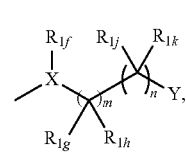

wherein only one of W and Z comprises hydrogen;

wherein, R1f, R1g, R1h, R1j and R1k are each independently selected from hydrogen, alkyl, alkenyl, hydroxyalkyl, thioalkyl, or aminoalkyl;

wherein m and n are independently whole numbers ranging from 0 to 5;

wherein X is selected from CH or N;

wherein Y is SR;

wherein R comprises H or a protected thiol group selected from the group consisting of isothiouronium, thioacetyl, thiotetrahydropyranyl, —C(NH$_2$)=NH$_2^+$A$^-$, a mercapto radical connected to another mercapto radical (Xa) or (Xa') to form a disulfide structure, and combinations thereof;

wherein A$^-$ is selected from the group consisting of bromide, chloride, iodide, sulfate, methanesulfonate, carbonate, phosphate, acetate, and combinations thereof.

Q. The compound according to Paragraph P, wherein the odorless thiol is represented by structure Xa and wherein R1b, R1c, and R1e are hydrogens.

R. The compound according to Paragraphs P-Q, wherein the odorless thiol is represented by structure Xa;

wherein W, R1b, R1c, R1e, R1f, R1g, R1h, R1j and R1k are hydrogens;

wherein X is N;
wherein m+n is equal to or larger than 1, preferably greater than or larger than 2.

S. The compound according to Paragraphs P-R, wherein the odorless thiol is represented by structure Xa;
wherein W, R1b, R1c, R1e R1f, R1g, R1h, R1j and R1k are hydrogens;
wherein X is N;
wherein m+n is equal to or larger than 1, preferably greater than or larger than 2;
wherein R1a is methyl;
wherein R is H or —C(NH$_2$)=NH$_2$$^+$A$^-$;
wherein A$^-$ is Br$^-$.

T. The compound according to Paragraphs P-S, wherein the odorless thiol is represented by structure Xa;
wherein the odorless thiol is represented by molecular structure Xa;
wherein W, R1b, R1c, R1e R1f, R1g, R1h, R1j and R1k are hydrogens;
wherein X is N;
wherein R1a is methyl;
wherein m is 1 and n is 2;
wherein R is H or —C(NH$_2$)=NH$_2$$^+$A$^-$;
and wherein A$^-$ is Br$^-$.

U. The compound according to Paragraphs P-T, wherein the odorless thiol is represented by structure Xa;
wherein W, R1b, R1c, R1e R1f, R1g, R1h, R1j and R1k are hydrogens;
wherein X is N;
wherein R1a is methyl;
wherein m and n are both equal to 2;
wherein R is H or —C(NH$_2$)=NH$_2$$^+$A$^-$;
and wherein A$^-$ is Br$^-$.

V. The compound according to Paragraphs P-U, wherein the odorless thiol is represented by structure Xa;
wherein W, R1b, R1c, R1e R1f, R1g, R1h, R1j and R1k are hydrogens;
wherein X is CH;
wherein m is 0 and n is 1.

W. The compound according to Paragraphs P-V, wherein the odorless thiol is represented by structure Xa;
wherein W, R, R1b, R1c, R1e R1f, R1g, R1h, R1j and R1k are hydrogens;
wherein X is CH;
wherein m is 0 and n is 1;
wherein R1a is methyl;
and wherein A$^-$ is Br$^-$.

X. The compound according to Paragraphs P-W, wherein the odorless thiol is represented by structure Xa;
wherein W, R1b, R1c, R1e R1f, R1g, R1h, R1j and R1k are hydrogens;
wherein X is CH;
wherein m is 0 and n is 1;
wherein R1a is methyl;
and wherein A$^-$ is Br$^-$;
wherein R is H or —C(NH$_2$)=NH$_2$$^+$A$^-$.

Y. The compound according to Paragraphs P-X, wherein the odorless thiol is represented by structure Xa';
wherein W, R, R1b, R1c, R1e, R1f, R1g, R1h, R1j and R1k are hydrogens;
wherein X is CH;
wherein L is —(CH$_2$)$_4$—;
A$^-$ is Br$^-$.

Z. The compound according to Paragraphs P-Y, wherein the odorless thiol is represented by structure Xa';
wherein W, R1b, R1c, R1e, R1f, R1g, R1h, R1j and R1k are hydrogens;
wherein X is CH;
wherein L is —(CH$_2$)$_4$—;
wherein R is H or —C(NH$_2$)=NH$_2$$^+$A$^-$;
wherein A$^-$ is Br$^-$.

AA. The compound according to Paragraphs P-Z, wherein the odorless thiol is represented by structure Xa and both W and Z are group T.

BB. The compound according to Paragraphs P-AA, wherein the odorless thiol is represented by structure Xa;
wherein R1b, R1c, R1e, R1f, R1g, R1h, R1j and R1k are hydrogens;
wherein X is N;
wherein m+n is equal to or larger than 1, preferably greater than or equal to 2;
wherein both W and Z groups are group T.

CC. The compound according to Paragraphs P-BB, wherein the odorless thiol is represented by structure Xa;
wherein R, R1b, R1c, R1e, R1f, R1g, R1h, R1j and R1k are hydrogens;
wherein both W and Z groups are group T;
wherein X is N;
wherein m and n are both 1;
wherein R1a is methyl;
and wherein A$^-$ is Br$^-$.

DD. The compound according to Paragraphs P-CC, wherein the odorless thiol is represented by structure Xa;
wherein R$_{1b}$, R$_{1c}$, R$_{1e}$, R$_{1f}$, R$_{1g}$, R$_{1h}$, R$_{1j}$ and R$_{1k}$ are hydrogens;
wherein both W and Z groups are group T;
wherein X is N;
wherein m and n are both 1;
wherein R$_{1a}$ is methyl;
wherein R is H or —C(NH$_2$)=NH$_2$$^+$A$^-$;
and wherein A$^-$ is Br$^-$.

EE. The compound according to Paragraphs P-DD, wherein the odorless thiol is represented by structure Xa;
wherein R1b, R1c, R1e, R1f, R1g, R1h, R1j and R1k are hydrogens,
wherein both W and Z groups are group T;
wherein X is CH;
wherein m is 0 and n is 1.

FF. The compound according to Paragraphs P-EE, wherein the odorless thiol is represented by structure Xa;
wherein R, R1b, R1c, R1e, R1f, R1g, R1h, R1j and R1k are hydrogens;
wherein both W and Z groups are group T;
wherein X is CH;
wherein R1a is methyl;
wherein m is 0 and n is 1;
and wherein A$^-$ is Br$^-$.

GG. The compound according to Paragraphs P-FF, wherein the odorless thiol is represented by structure Xa;
wherein R1b, R1c, R1e, R1f, R1g, R1h, R1j and R1k are hydrogens;
wherein both W and Z groups are group T;
wherein X is CH;
wherein R$_{1a}$ is methyl;
wherein m is 0 and n is 1;
wherein R is —C(NH$_2$)=NH$_2$$^+$A$^-$;
and wherein A$^-$ is Br$^-$.

HH. A permanent styling composition comprising from about 0.5% to about 20%, preferably from about 1% to about 15%, more preferably from about 3% to about 12%, and most preferably from about 5% to about 12% of the odorless thiol according to Paragraphs P-GG.

II. A depilatory composition comprising from about 1% to about 20%, preferably from about 3% to about 18%, and more preferably from about 5% to about 15% of the odorless thiol of according to Paragraphs P-HH.

JJ. A method of treating hair to permanently shape hair comprising the steps:
(a) putting the hair in a desired shape,
(b) before and/or after the hair is put in the desired shape, applying a permanent styling composition according to Paragraphs P-II, to the hair,
(c) rinsing the reducing composition from the hair;
(d) applying an oxidizing composition to the hair comprising:
(i) from about 0.5% to about 12% of an oxidizing agent, by weight of the oxidizing composition; and
(ii) from about 80% to about 97% of a solvent, by weight of the oxidizing composition; and
(e) rinsing the oxidizing composition from the hair.

KK. A method of removing hair from a bodily surface comprising the steps:
(a) applying the composition of according to Paragraphs P-II, to the bodily surface where it is desired to remove hair,
(b) leaving the composition on the bodily surface for about 1 to about 15 minutes, preferably from about 3 to about 10 minutes, and more preferably from about 5 to about 7 minutes; and
(c) removing the composition from the bodily surface.

LL. Use of the odorless thiol compound having one of the following structure of formula Xa or Xa' of claim 1 for hair removal.

MM. Use of the odorless thiol compound having one of the following structure of formula Xa or Xa' of claim 1 for permanently shaping hair.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An odorless thiol compound comprising a pyridinium ring of the following structure of formula Xa or:

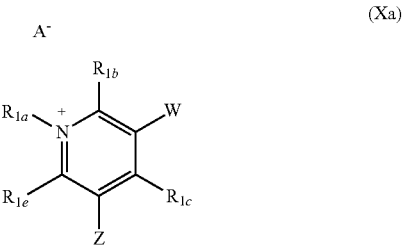

wherein $R_{1a}$ is:
a linear, branched, cyclo alkyl, aminoalkyl, hydroxyalkyl or alkenyl group,
or a linker group L which connects to another moiety of Xa forming a dimeric structure;
wherein the linker group L is a linear, branched or cyclo alkyl, aminoalkyl,
hydroxyalkyl or alkenyl group;
wherein $R_{1b}$, $R_{1c}$, and $R_{1e}$ are each independently selected from hydrogen, alkyl, alkenyl, alkynyl, aryl, hydroxyalkyl, aminoalkyl, acyl, or a heterocyclic moiety;
wherein W and Z are different and are hydrogen or a group T; or W and Z are the same and are the group T represented by the structure:

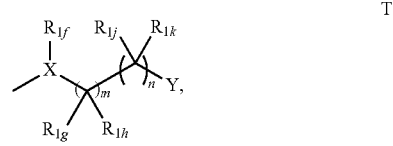

wherein the group T is attached to the pyridinium ring through X;
wherein, $R_{1f}$, $R_{1g}$, $R_{1h}$, $R_{1j}$ and $R_{1k}$ are each independently selected from hydrogen, alkyl, alkenyl, hydroxyalkyl, thioalkyl, or aminoalkyl;
wherein m and n are independently whole numbers ranging from O to 5;
wherein X is selected from N;
wherein Y is SR;
wherein R comprises H or a protected thiol group selected from the group consisting of isothiouronium, thioacetyl, thiotetrahydropyranyl, —C($NH_2$)=$NH_2^+A^-$, a mercapto radical connected to another mercapto radical (Xa) to form a disulfide structure, and combinations thereof;
wherein $A^-$ is selected from the group consisting of bromide, chloride, iodide, sulfate, methanesulfonate, carbonate, phosphate, acetate, and combinations thereof.

2. The compound of claim 1 wherein the odorless thiol is represented by structure Xa and wherein $R_{1b}$, $R_{1c}$, and $R_{1e}$ are hydrogens.

3. The compound of claim 1 wherein the odorless thiol is represented by structure Xa;
wherein W, $R_{1b}$, $R_{1c}$, $R_{1e}$, Rif, $R_{1g}$, $R_{1h}$, $R_{1j}$ and $R_{1k}$ are hydrogens;
wherein X is N;
wherein m and n are independently whole numbers ranging from 0 to 5.

4. The compound of claim 1 wherein the odorless thiol is represented by structure Xa;
  wherein W, $R_{1b}$, $R_{1c}$, $R_{1e}$ Rif, $R_{1g}$, $R_{1h}$, $R_{1j}$ and $R_{1k}$ are hydrogens;
  wherein X is N;
  wherein m and n are independently whole numbers ranging from 0 to 5;
  wherein $R_{1a}$ is methyl;
  wherein R is H or —$C(NH_2)=NH_2^+A^-$;
  wherein $A^-$ is $Br^-$.

5. The compound of claim 1 wherein the odorless thiol is represented by structure Xa;
  wherein W, $R_{1b}$, $R_{1c}$, $R_{1e}$, Rif, $R_{1g}$, $R_{1h}$, $R_{1j}$ and $R_{1k}$ are hydrogens;
  wherein X is N;
  wherein $R_{1a}$ is methyl;
  wherein m is 1 and n is 2;
  wherein R is H or —$C(NH_2)=NH_2^+A^-$;
  and wherein $A^-$ is $Br^-$.

6. The compound of claim 1 wherein the odorless thiol is represented by structure Xa;
  wherein W, $R_{1b}$, $R_{1c}$, $R_{1e}$ Rif, $R_{1g}$, $R_{1h}$, $R_{1j}$ and $R_{1k}$ are hydrogens;
  wherein X is N;
  wherein $R_{1a}$ is methyl;
  wherein m and n are both equal to 2;
  wherein R is H or —$C(NH_2)=NH_2^+A^-$;
  and wherein $A^-$ is $Br^-$.

7. The compound of claim 1 wherein the odorless thiol is represented by structure Xa and both W and Z are group T.

8. The compound of claim 1 wherein the odorless thiol is represented by structure Xa;
  wherein R, $R_{1b}$, $R_{1c}$, $R_{1e}$, $R_{1f}$, $R_{1g}$, $R_{1h}$, $R_{1j}$ and $R_{1k}$ are hydrogens;
  wherein X is N;
  wherein m and n are independently whole numbers ranging from 0 to 5;
  wherein both W and Z groups are group T.

9. The compound of claim 1 wherein the odorless thiol is represented by structure Xa;
  wherein R, $R_{1b}$, $R_{1c}$, $R_{1e}$, Rif, $R_{1g}$, $R_{1h}$, $R_{1j}$ and $R_{1k}$ are hydrogens;
  wherein both W and Z groups are group T;
  wherein X is N;
  wherein m and n are both 1;
  wherein $R_{1a}$ is methyl;
  and wherein $A^-$ is $Br^-$.

10. The compound of claim 1 wherein the odorless thiol is represented by structure Xa;
  wherein $R_{1b}$, $R_{1c}$, $R_{1e}$, $R_{1f}$, $R_{1g}$, $R_{1h}$, $R_{1j}$ and $R_{1k}$ are hydrogens;
  wherein both W and Z groups are group T;
  wherein X is N;
  wherein m and n are both 1;
  wherein $R_{1a}$ is methyl,
  wherein R is H or —$C(NH_2)=NH_2^+A^-$;
  and wherein $A^-$ is $Br^-$.

11. A permanent styling composition or a depilatory composition comprising from about 1% to about 20% of the odorless thiol of claim 1, by weight of the permanent styling composition or a depilatory composition.

12. A method of treating hair to permanently shape hair comprising the steps:
  (a) putting the hair in a desired shape,
  (b) before and/or after the hair is put in the desired shape, applying the permanent styling composition of claim 11 to the hair,
  (c) rinsing the permanent styling composition from the hair;
  (d) applying an oxidizing composition to the hair comprising:
    (i) from about 0.5% to about 12% of an oxidizing agent, by weight of the oxidizing composition; and
    (ii) from about 80% to about 97% of a solvent, by weight of the oxidizing composition; and
  (e) rinsing the oxidizing composition from the hair.

* * * * *